(12) United States Patent
Han et al.

(10) Patent No.: US 6,932,603 B2
(45) Date of Patent: Aug. 23, 2005

(54) INTERPROXIMAL SQUIRT BRUSH

(76) Inventors: Johnny Steve Han, 1830 Debann Pl., Rowland Heights, CA (US) 91748; Mei-Ling Pauling Han, 1830 Debann Pl., Rowland Heights, CA (US) 91748

( * ) Notice: Subject to any disclaimer, the term of this patent is extended or adjusted under 35 U.S.C. 154(b) by 22 days.

(21) Appl. No.: 10/637,116

(22) Filed: Aug. 8, 2003

(65) Prior Publication Data

US 2005/0032019 A1 Feb. 10, 2005

(51) Int. Cl.[7] .......................... A61C 17/00; A47L 13/22
(52) U.S. Cl. .......................................... 433/80; 401/290
(58) Field of Search .......................... 433/80, 215, 82; 15/167.1, 176.1; 401/185, 28, 268, 290; 222/569, 192; 132/112

(56) References Cited

U.S. PATENT DOCUMENTS

| | | | | |
|---|---|---|---|---|
| 2,226,814 A | * | 12/1940 | Gregg | 15/145 |
| 2,761,163 A | * | 9/1956 | Domino | 15/176.1 |
| 3,174,174 A | * | 3/1965 | Dengler | 401/25 |
| 4,780,923 A | | 11/1988 | Schultheiss | |
| 4,828,420 A | * | 5/1989 | Otsuka et al. | 401/268 |
| 4,875,602 A | * | 10/1989 | Chickering et al. | 222/187 |
| 5,150,495 A | * | 9/1992 | Discko et al. | 15/167.1 |
| 5,330,357 A | * | 7/1994 | Keller | 433/215 |
| 5,383,924 A | | 1/1995 | Brehier | |
| 5,488,751 A | | 2/1996 | Gekhter | |
| 5,702,686 A | | 12/1997 | Maekawa | |
| 5,775,572 A | * | 7/1998 | Oliff | 229/120.03 |
| 5,829,976 A | | 11/1998 | Green | |
| D406,193 S | | 3/1999 | Steinmann | |
| 5,882,584 A | | 3/1999 | Tsurukawa | |
| 6,015,293 A | | 1/2000 | Rimkus | |
| 6,082,999 A | | 7/2000 | Tcherny | |
| 6,220,773 B1 | | 4/2001 | Wiegner | |
| D445,186 S | | 7/2001 | Mangione | |
| 6,325,626 B1 | | 12/2001 | Blass | |
| 2003/0224320 A1 | * | 12/2003 | Kandelman et al. | 433/80 |

* cited by examiner

Primary Examiner—Cary E. O'Connor
(74) Attorney, Agent, or Firm—Raymond Y. Chan; David and Raymond

(57) ABSTRACT

An interproximal squirt brush includes a squeezable bottle having a solution cavity for containing a washing solution and a nozzle head having an opening, and a brush head including a brush arm and a brush member. The brush arm has a brush portion and a resilient portion slidably inserted into the opening of the squeezable bottle for providing an urging force against an inner wall of the nozzle head, wherein a dispensing channel is formed between the resilient portion of the brush arm and the inner wall of the nozzle head for allowing the washing solution to pass therethrough. The brush member is provided at the brush portion of the brush arm. Therefore, when a squeezing force is applied on the squeezable bottle, the washing solution is released to the brush member through the dispensing channel of the nozzle head.

7 Claims, 5 Drawing Sheets

INTERPROXIMAL SQUIRT BRUSH

BACKGROUND OF THE PRESENT INVENTION

1. Field of Invention

The present invention relates to a dental instrument, and more particularly to an interproximal squirt brush, which can substantially clean and remove stains between teeth and around implants by both physical therapy and chemical treatment.

2. Description of Related Arts

Gum disease (periodontitis) is one of the common dental problems. Periodontal disease, especially in the early stages, is usually not painful such that many people having gum disease do not even realize it. Researches report that the periodontal disease is an infection in the gums caused by the bacteria in plaque, wherein plaque and bacteria build up on and between the teeth. To prevent the gum disease, dentists always suggest having a better oral hygiene by brushing and flossing regularly. In addition, mouthwash is also considered as one of the effective methods for removing plaque and bacteria. By reducing the amount of plaque on your teeth, you can reduce the amount of bacteria in your mouth.

Brushing method is the most common method for removing plaque built-up on the teeth. However, due to the structure of the toothbrush, the bristles of the toothbrush cannot effectively remove the plaque from the areas between teeth and around the gums. Therefore, flossing becomes the effective way to help the user to remove plaque and debris from between the teeth, especially the areas inaccessible to the toothbrush. It is ideal to use the mouthwash after brushing and/or flossing since the mouthwash with medicament is capable of not only effectively removing oral bacteria and stain on the teeth but also reducing bad breath.

However, the flossing technique of holding the floss by hand leads to different operational result depending on the users. Flossing requires the user to floss up, down, right, left, front, and back. This six-step process is too cumbersome and time consuming. Therefore, the conventional floss is disadvantageous in practical use. An improved toothpick, which combines the advantages of both toothbrush, floss, and mouthwash, comprises a brush head having a size adapted to fit between the teeth and gum line to brush the areas thereof. Due to the friction between the brush head and the gum line, tenderness during dry brushing always gives discomfort to the user. An improper brushing the gum line may even cause the gum bleeding.

SUMMARY OF THE PRESENT INVENTION

The main object of the present invention is to provide an interproximal squirt brush, which can substantially clean and remove stains between teeth and around implants by both physical therapy and chemical treatment.

Another object of the present invention is to provide an interproximal squirt brush, wherein a user is able to use the interproximal squirt brush with mouthwash, which combines the flossing and mouthwash techniques, in one step to remove oral bacteria between the gums and teeth, stain and plaque built on the teeth, and to reduce bad breath at the same time.

Another object of the present invention is to provide an interproximal squirt brush, wherein the washing solution is guided to apply on the brush head such that when the brush head fits between the teeth and gum line during brushing process, the washing solution not only penetrates through the area between the teeth and around the gum line to remove the stain and bad breath, but also functions as a lubricant to minimize the friction between the brush member and the gum line so as to prevent gum bleed and uncomfortable feeling to the user. In other words, the washing solution, such as medicament, can be used for the present invention to control infection between the gums thus preventing the growth of gum disease.

Another object of the present invention is to provide an interproximal squirt brush, wherein the brush head has a resilient portion inserted into an opening of the squeezable bottle to retain the brush head in position such that the washing solution contained in the squeezable bottle can be substantially applied on the brush head by a squeezing force applied on the squeezable bottle. Accordingly, there are additional shapes, animal characters, and sizes for the squeezable bottle that can be attached to the brush head, such as the elongating and shrinking brush end.

Another object of the present invention is to provide an interproximal squirt brush, wherein the cleaning operation is easy and simple by fitting the brush head between the teeth and around gum line to brush therewith and by squeezing the washing solution towards the brush head.

Another object of the present invention is to provide an interproximal squirt brush, wherein not only the brush head is replaceably mounted to the squeezable bottle but also the washing solution can be refilled into the squeezable bottle so as to extend the service life span of the interproximal squirt brush of the present invention. For example, the washing solution can be easily replaced by removing a rubber stopper at the bottom of the squeezable bottle.

Another object of the present invention is to provide an interproximal squirt brush, wherein no expensive or complicated structure is required to employ in the present invention in order to achieve the above mentioned objects. Therefore, the present invention successfully provides an economic and efficient solution not only for removing plaque and stain on the teeth through the flossing technique but also for reducing oral bacteria and bad breath through the mouthwash technique.

Accordingly, in order to accomplish the above objects, the present invention provides an interproximal squirt brush, comprising:

a squeezable bottle having a solution cavity for containing a washing solution and a hollow nozzle head having an opening communicating with the solution cavity; and a brush head, comprising:

an elongated brush arm having a brush portion and a resilient portion slidably inserted into the opening of the squeezable bottle for providing an urging force against an inner wall of the nozzle head, so as to hold the brush arm in position, wherein a dispensing channel is formed between the resilient portion of the brush arm and the inner wall of the nozzle head for allowing the washing solution to pass towards the brush portion of the brush arm through the nozzle head; and a brush member provided at the brush portion of the brush arm, thereby, when a squeezing force is applied on the squeezable bottle, the washing solution is released to deliver to the brush member through the dispensing channel of the nozzle head.

These and other objectives, features, and advantages of the present invention will become apparent from the following detailed description, the accompanying drawings, and the appended claims.

DETAILED DESCRIPTION OF THE PREFERRED EMBODIMENT

Figure 1:
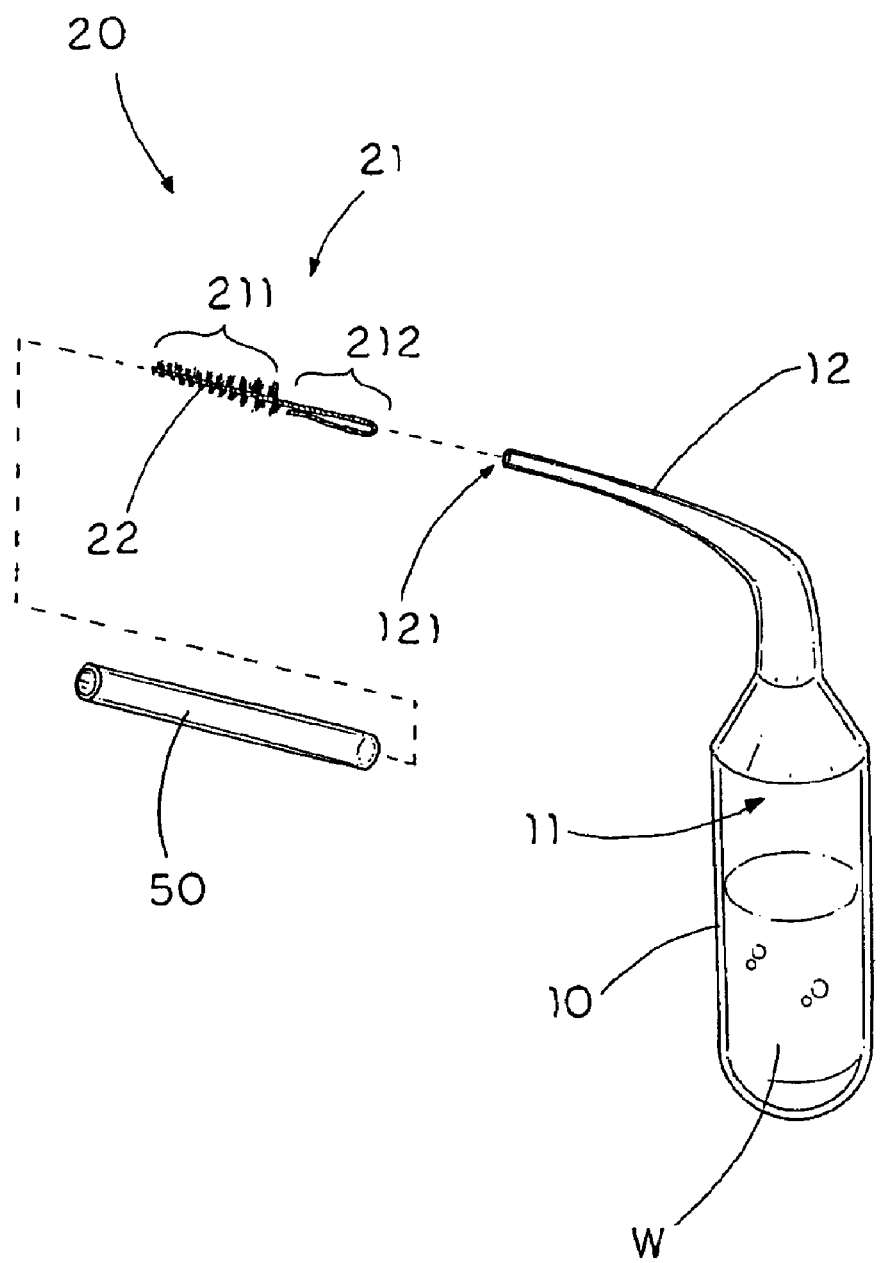
FIG. 1 is a perspective view of an interproximal squirt brush according to a preferred embodiment of the present invention.
Figure 2:
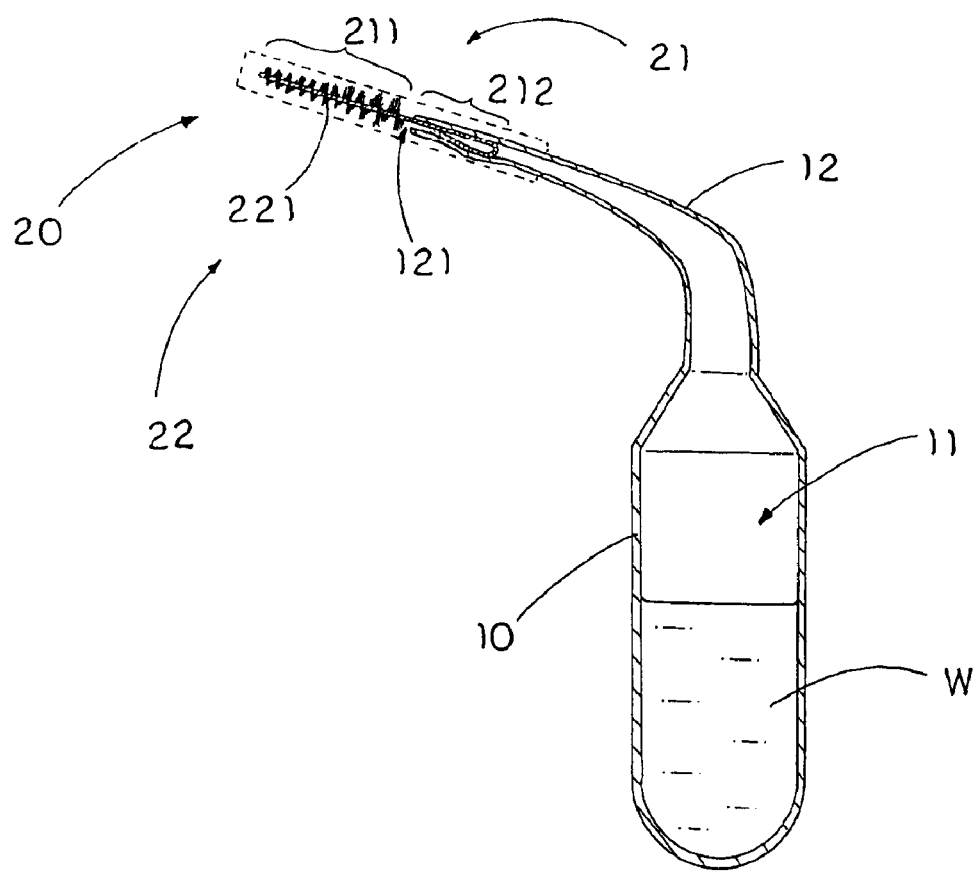
FIG. 2 is a side sectional view of the interproximal squirt brush according to the above preferred embodiment of the present invention.
Figure 3:
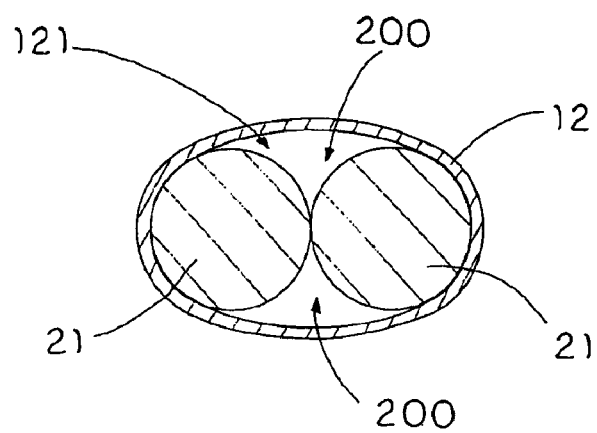
FIG. 3 is a front sectional view of the interproximal squirt brush according to the above preferred embodiment of the present invention.

Referring to FIGS. 1 through 3 of the drawings, an interproximal squirt brush according to a preferred embodiment of the present invention is illustrated, wherein the interproximal squirt brush comprises a squeezable bottle 10 and a brush head 20 comprising an elongated brush arm 21 and a brush member 22.

The squeezable bottle 10 has a solution cavity 11 for containing a washing solution W and a hollow nozzle head 12 having an opening 121 communicating with the solution cavity 11.

The brush arm 21 of the brush head 20 has a brush portion 211 and a resilient portion 212 slidably inserted into the opening 121 of the squeezable bottle 10 for providing an urging force as a locking force against an inner wall of the nozzle head 12, so as to hold the brush arm 21 in position, wherein a dispensing channel 200 is formed between the resilient portion 212 of the brush arm 21 and the inner wall of the nozzle head 12 for allowing the washing solution W to pass towards the brush portion 211 of the brush arm 21 through the nozzle head 12.

The brush member 22 is provided at the brush portion 211 of the brush arm 21, thereby, when a squeezing force is applied on the squeezable bottle 10, the washing solution W is released to deliver to the brush member 22 through the dispensing channel 200 of the nozzle head 12.

According to the preferred embodiment, the squeezable bottle 10 is preferably made of plastic such that a user is able to squeeze the squeezable bottle 10 to dispense the washing solution W in the solution cavity 11 through the opening 121 of the nozzle head 12. The nozzle head 12 is constructed to have a supportive and rigid structure to substantially support the brush head 20 so as to prevent the nozzle head 12 from being bent when the brush head 20 fits between the teeth during the brushing operation. Accordingly, the nozzle head 12 is integrally extended from the bottle body 10 to communicate with the solution cavity 11. The squeezable bottle 10 is embodied as a one-piece integral member adapted to be made by injection molding techniques, so as to minimize the manufacturing cost of the interproximal squirt brush of the present invention.

Figure 4:
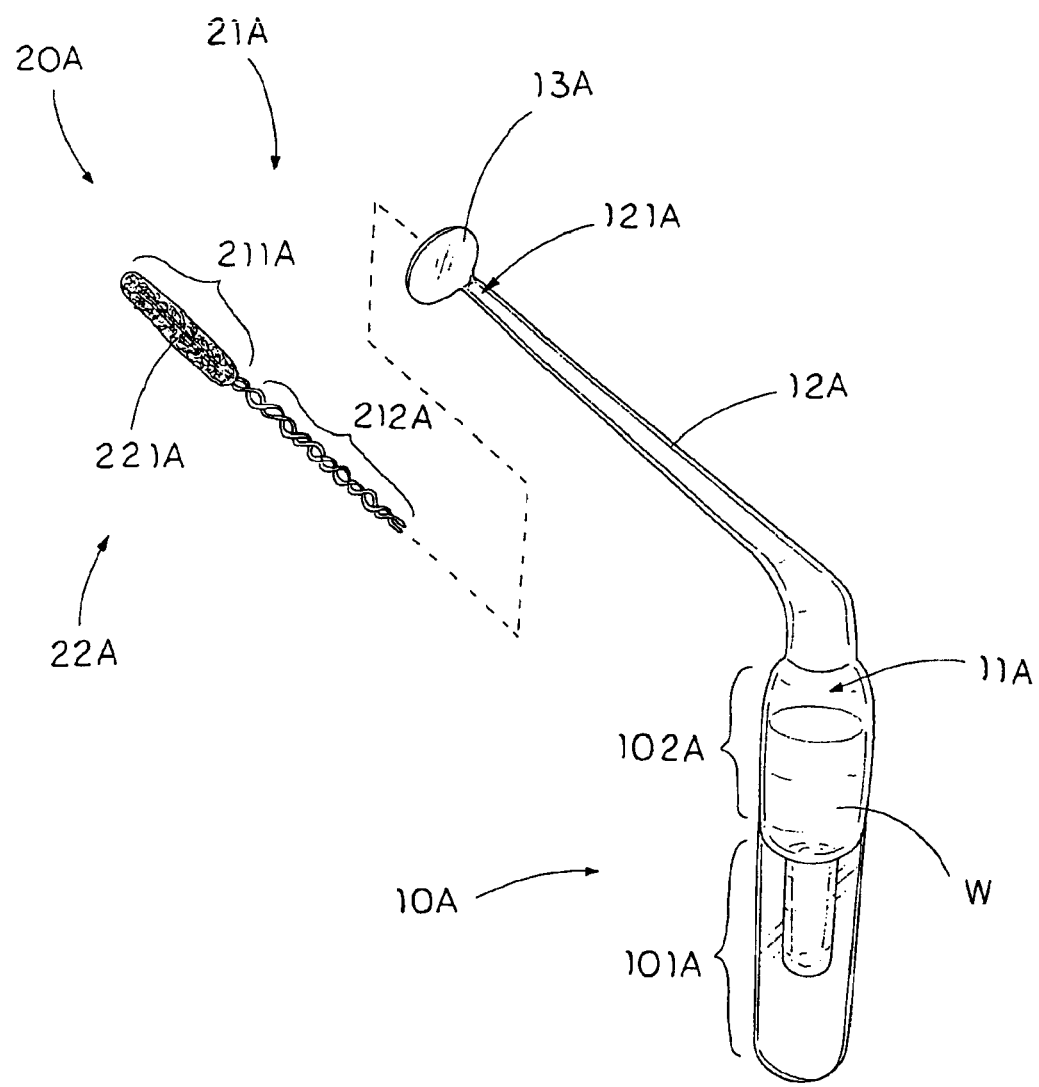
FIG. 4 illustrates a first alternative mode of a brush head of the interproximal squirt brush according to the above preferred embodiment of the present invention.

Alternatively, the squeezable bottle 10A has a handle portion 101A and a squeezing portion 102A, as shown in FIG. 4, wherein the squeezable bottle 10A further has a sealing cap 13A sealedly mounted at the opening 121A of the squeezable bottle 10A for retaining a predetermined volume of washing solution W in the solution cavity 11A. Therefore, the user is able to tear off the sealing cap 13A and insert the brush head 20A into the opening 121A of the squeezable bottle 10A. In other words, the interproximal squirt brush is well suit for disposable one-time use.

Accordingly, the washing solution W can be water or medicament commonly sold in market for removing oral bacteria and bad breath. It is worth to mention that the user is able to squeeze the squeezable bottle 10 to suck the washing solution W into the solution cavity 11 to refill the washing solution W.

The brush head 20, according to the preferred embodiment, is an interproximal brush arranged to fit between the teeth and around the gum line of the user so as to clean the teeth and massage the gum. As shown in FIG. 1, the brush head 20 is replaceably mounted to the squeezable bottle 10 such that the user is able to replace the used brush head 20 from the squeezable bottle 10 with a new brush head 20 by inserting the brush head 20 into the opening 121 of the squeezable bottle 10.

The brush arm 21, which is made of bendable material such as metal wire, is a wiring arm wherein the resilient portion 212 of the brush arm 21, having a loop shaped, is formed by bending a tail portion of the wiring arm to form a U-shaped structure in such a manner that when the resilient portion 212 of the brush arm 21 is slidably inserted into the opening 121 of the squeezable bottle 10, the resilient portion 212 of the brush arm 21 is arranged to bias against the inner wall of the nozzle head 12 so as to hold the brush head 20 in position, as shown in FIG. 2.

As shown in FIG. 3, a diameter of the opening 121 is slightly smaller than a width of the resilient portion 212 of the brush arm 21 such that when the resilient portion 212 of the brush arm 21 is inserted into the opening 121 of the squeezable bottle 10, the resilient portion 212 of the brush arm 21 biases against the inner wall of the nozzle head 12 to slightly deform a shape of the nozzle head 12. In other words, the resilient portion of the brush arm 21 provides the urging force as the locking force to securely retain the brush head 20 in position.

In addition, the dispensing channel 200 is a clearance between the resilient portion 212 of the brush arm 21 and the inner wall of the nozzle head 12 wherein the dispensing channel 200 is capable of allowing the washing solution W passing therethrough towards the brush portion 211 of the brush arm 21.

The brush member 22, according to the preferred embodiment, comprises a plurality of wire bristles 221 radially extended from the brush portion 211 of the brush arm 21 for fitting between the teeth and around the gum line to perform the brushing and/or flossing action so as to remove the stain and plaque on the teeth, as shown in FIG. 1. In addition, when the squeezing force is applied on the squeezable bottle 10, the washing solution W is delivered to the wire bristles 221 of the brush member 22 through the dispensing channel 200 of the nozzle head 12. Therefore, when the brush member 22 fits between the teeth and gum line during brushing process, the washing solution W not only penetrates through the area between the teeth and around the gum line to remove the stain and bad breath, but also functions as a lubricant to minimize the friction between the brush member 22 and the gum line so as to control gum disease and reduce uncomfortable feeling to the user.

It is worth to mention that when the brush member 22 fits between the teeth or around the gum line, the opening 121 of the nozzle head 12 is guided to point at the gap between the teeth or the gum line. Therefore, the user is able to precisely deliver the washing solution W towards the gap between the teeth and/or the gum while the brush member 22 is located.

As shown in FIG. 1, the interproximal squirt brush further comprises a tubular protective cap 50 having a predetermined length to receive the brush head 20 therein wherein the nozzle head 12 is slidably inserted into the protective cap 50 so as to protectively cover the brush head 20 within the protective cap 50.

FIG. 4 illustrates an alternative mode of the brush head 20A which comprises the brush arm 21A having the resilient portion 212A slidably inserted into the opening 121A of the squeezable bottle 10A, and the brush member 22A provided at the brush portion 211A of the brush arm 21A.

The brush arm 21A, which is made of bendable material such as metal wire, is a wiring arm wherein the resilient portion 212A of the brush arm 21A is formed by bending a tail portion of the wiring arm to form a U-shaped structure and then twisting the tail portion of the wiring arm in continuous "8" shaped in such a manner that when the resilient portion 212A of the brush arm 21A is slidably inserted into the opening 121A of the squeezable bottle 10A, the resilient portion 212A of the brush arm 21A is arranged to bias against the inner wall of the nozzle head 12A so as to hold the brush head 20A in position, as shown in FIG. 4.

The brush member 22A comprises a scrub element 221A attached around the brush portion 211A of the brush arm 21A, as shown in FIG. 4, wherein the scrub element 221A is a fibrous material such as nylon, polyurethane foam or polyolefins. In other words, the washing solution W is delivered to the scrub element 221A of the brush member 22A to clean the teeth and enhance the scrubbing process.

Figure 5:
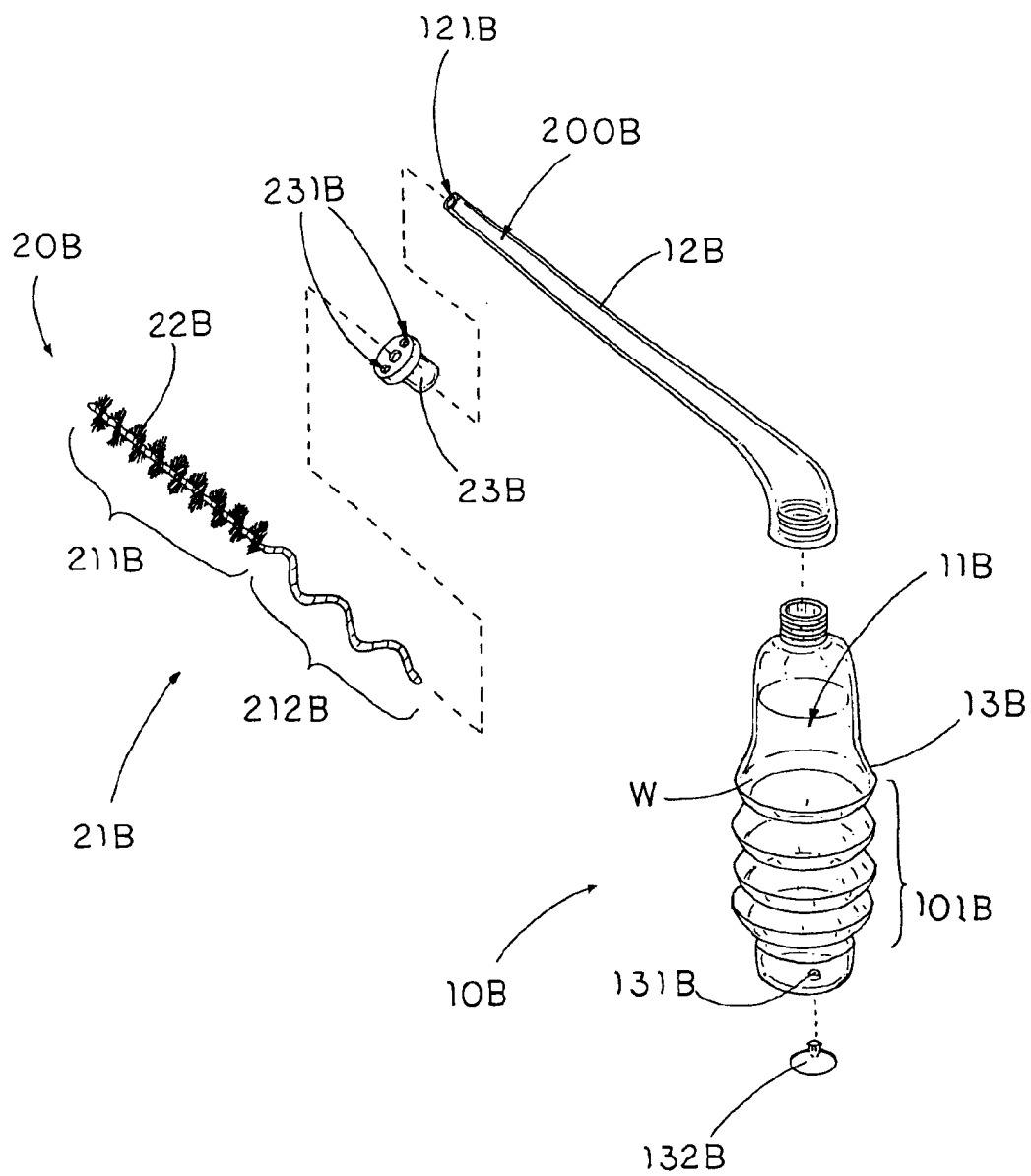
FIG. 5 illustrates a second alternative mode of the brush head of the interproximal squirt brush according to the above preferred embodiment of the present invention.

FIG. 5 illustrates a second alternative mode of the interproximal squirt brush wherein the brush arm 21B of the brush head 20B has the resilient portion 212B slidably inserted into the opening 121B of the squeezable bottle 10B and the brush portion 211B where the brush member 22B is provided thereon.

The brush arm 21B, which is made of bendable material such as metal wire, is a wiring arm wherein the resilient portion 212B of the brush arm 21B is formed by twisting a tail portion of the wiring arm into a snake-liked manner in such a manner that when the resilient portion 212B of the brush arm 21B is slidably inserted into the opening 121B of the squeezable bottle 10B, the resilient portion 212B of the brush arm 21B is arranged to bias against the inner wall of the nozzle head 12B so as to hold the brush head 20B in position, as shown in FIG. 5.

The squeezable bottle 10B further comprises a bottle body 13B defining the solution cavity 11B therein wherein the nozzle head 12B is detachably attached to the bottle body 13B to communicate the opening 121B of the nozzle head 12B with the solution cavity 11B. As shown in FIG. 5, the bottle body 13B has a threaded portion formed at an opening portion of the bottle body 13B and the nozzle head 12B has a corresponding threaded portion rotatably engaged with the threaded portion of the bottle body 13B so as to detachably attach the nozzle head 12B to the bottle body 13B for delivering the washing solution W from the solution cavity 11B to the opening 121B of the nozzle head 12B.

In addition, the bottle body 13B further has a squeezable accordion style handle portion 101B allowed to be squeezed for delivering the washing solution W from the solution cavity 11B to the opening 121B of the nozzle head 12B. In other words, the squeezable bottle 10B can be made of any shape and size that can be squeezed for dispensing the washing solution W. The bottle body 13B further has a refilling opening 131B formed at a bottom side thereof and comprises a rubber made stopper 132B detachably mounted to the bottle body 13B at the refilling opening 131B in such a manner that the washing solution W can be refilled into the solution cavity 11B through the refilling opening 131B when the stopper 132B is detached therefrom.

It is worth to mention that the brush head 20B can be permanently attached to the nozzle head 12B while the nozzle head 12B is detachably attached to the bottle body 13B. In other words, the replacement of the brush head 20B is easily replaced by a new nozzle head 12B with a new brush head 20B as a whole to the bottle body 13B.

As shown in FIG. 5, the brush head 20B further comprises a liquid guider 23B, having at least a dispensing hole 231B, mounted on the brush arm 21B wherein when the resilient portion 212B is slidably inserted into the nozzle head 12B, the liquid guider 23B is attached to the opening 121B of the nozzle 12B to communicate the dispensing hole 231B with the solution cavity 11B for delivering the washing solution W from the solution cavity 11B to outside through the dispensing hole 231B. Accordingly, when the squeezing force is applied on the squeezable bottle 10B, the washing solution W is released not only towards the brush member 22B at a position between the teeth through the dispensing channel 200B but also towards the gum around the brush member 22B through the dispensing hole 231B of the liquid guider 23B. In other words, the area in the oral cavity to be washed can be substantially increased by the liquid guider 23B.

Figure 6:
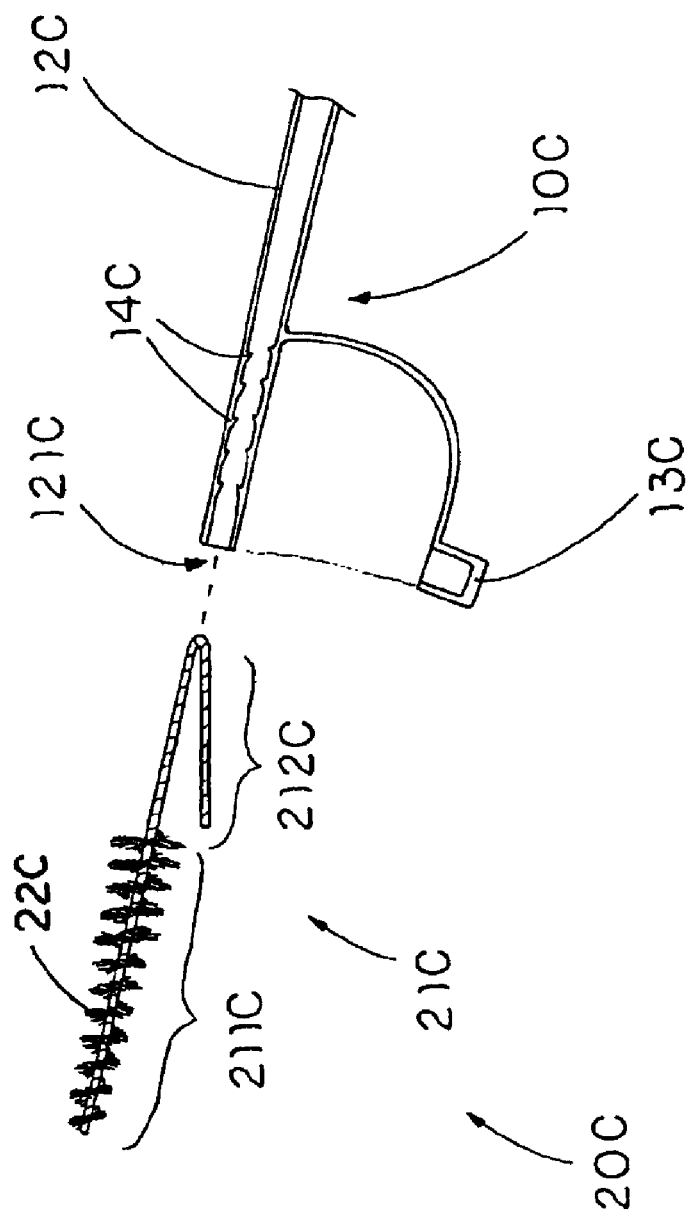
FIG. 6 illustrates a third alternative mode of the brush head of the interproximal squirt brush according to the above preferred embodiment of the present invention.

FIG. 6 illustrates a third alternative mode of the brush head 20C wherein the brush arm 21C has the resilient portion 212C slidably inserted into the opening 121C of the squeezable bottle 10C and the brush portion 211C where the brush member 22C is provided thereon.

The brush arm 21C, which is made of bendable material such as metal wire, is a wiring arm wherein the resilient portion 212C of the brush arm 21B is formed by bending a tail portion of the wiring arm into a V-shaped manner in such a manner that when the resilient portion 212C of the brush arm 21C is slidably inserted into the opening 121C of the squeezable bottle 10C, the resilient portion 212C of the brush arm 21C is arranged to bias against the inner wall of the nozzle head 12C so as to hold the brush head 20C in position, as shown in FIG. 6.

The squeezable bottle 10C further has at least a locking latch 14C integrally protruded from the inner wall of the nozzle head 12C to engage with the resilient portion 212C of the brush arm 21C so as to lock up the brush member 22C at the opening 121C of the squeezable bottle 10C. Accordingly, in order to lock up the brush head 20C with the squeezable bottle 10C, the resilient portion 212C of the brush arm 21C is slidably inserted into the nozzle head 12C of the squeezable bottle 10C until a free end of the wiring arm of the brush arm 21C is biased against the locking latch 14C of the nozzle head 12C so as to block the brush head 20C from sliding out of the nozzle head 12C. For removing the brush head 20C from the squeezable bottle 10C, the user is able to apply a squeezing force on the nozzle head 12C until the free end of the wiring arm is moved offset to the locking latch 14C such that the user is able to slide the brush head 20C out of the nozzle head 12C.

In addition, a covering cap 13C can be used to detachably cover on the opening 121C of the nozzle head 12C such that the squeezable bottle 10C can be re-used to refill the washing solution W therein.

It is worth to mention that the interlocking configuration of the squeezable bottle 10C having the locking latch 14C can be also used for the brush head 20, 20A as shown in FIGS. 1 and 4 in addition to any other brush head products.

In view of above, the alternative modes of the squeezable bottles 10, 10A, the brush head 20, 20A, 20B, 20C, and the liquid guider 23B can be interchanged to fit the use of the user. The size of the interproximal squirt brush of the present invention is relative small that can be stored and packed in luggage for travel or taken daily on one's person, in a handbag, or in a backpack in case of an emergency wherein one must clean one's teeth.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure form such principles. Therefore, this invention includes all modifications encompassed within the spirit and scope of the following claims.

What is claimed is:

1. An interproximal squirt brush, comprising:

a squeezable bottle having a solution cavity for containing a washing solution and a hollow nozzle head having an opening communicating with said solution cavity, wherein said squeezable bottle further has at least a locking latch integrally protruded from said inner wall of said nozzle head; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein said brush arm comprises a wiring arm, wherein said resilient portion of said brush arm is formed by bending a tail portion of said wiring arm into a V-liked manner, wherein said resilient portion of said brush arm is slidably inserted into said nozzle head of said squeezable bottle until a free end of said wiring arm of said brush arm is biased against said locking latch of said nozzle head so as to block said brush head from sliding out of said nozzle head; and a brush member provided at said brush portion of said brush arm, thereby, when a squeezing force is applied on said squeezable bottle, said washing solution is released to deliver to said brush member through said dispensing channel of said nozzle head.

2. An interproximal squirt brush, comprising:

a squeezable bottle having a solution cavity for containing a washing solution and a hollow nozzle head having an opening communicating with said solution cavity, wherein said squeezable bottle further has at least a locking latch integrally protruded from said inner wall of said nozzle head; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein a diameter of said opening is slightly smaller than a width of said resilient portion of said brush arm such that when said resilient portion of said brush arm is inserted into said opening of said squeezable bottle, said resilient portion of said brush arm biases against said inner wall of said nozzle head to slightly deform a shape of said nozzle head, wherein said brush arm comprises a wiring arm, wherein said resilient portion of said brush arm is formed by bending a tail portion of said wiring arm into a V-liked manner, wherein said resilient portion of said brush arm is slidably inserted into said nozzle head of said squeezable bottle until a free end of said wiring arm of said brush arm is biased against said locking latch of said nozzle head so as to block said brush head from sliding out of said nozzle head; and a brush member provided at said brush portion of said brush arm, thereby, when a squeezing force is applied on said squeezable bottle, said washing solution is released to deliver to said brush member through said dispensing channel of said nozzle head.

3. An interproximal squirt brush, comprising:

a squeezable bottle having a solution cavity for containing a washing solution and a hollow nozzle head having an opening communicating with said solution cavity, wherein said squeezable bottle further has at least a locking latch integrally protruded from said inner wall of said nozzle head; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein a diameter of said opening is slightly smaller than a width of said resilient portion of said brush arm such that when said resilient portion of said brush arm is inserted into said opening of said squeezable bottle, said resilient portion of said brush arm biases against said inner wall of said nozzle head to slightly deform a shape of said nozzle head, wherein said dispensing channel is a clearance between said resilient portion of said brush arm and said inner wall of said nozzle head, wherein said dispensing channel is capable of allowing said washing solution passing therethrough towards said brush portion of said brush arm, wherein said brush arm comprises a wiring arm, wherein said resilient portion of said brush arm is formed by bending a tail portion of said wiring arm into a V-liked manner, wherein said resilient portion of said brush arm is slidably inserted into said nozzle head of said squeezable bottle until a free end of said wiring arm of said brush arm is biased against said locking latch of said nozzle head so as to block said brush head from sliding out of said nozzle head; and a brush member provided at said brush portion of said brush arm, thereby, when a squeezing force is applied on said squeezable bottle, said washing solution is released to deliver to said brush member through said dispensing channel of said nozzle head.

4. An interproximal squirt brush, comprising:

a squeezable bottle having a solution cavity for containing a washing solution and a hollow nozzle head having an opening communicating with said solution cavity; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein a diameter of said opening is slightly smaller than a width of said resilient portion of said brush arm such that when said resilient portion of said brush arm is inserted into said opening of said squeezable bottle, said resilient portion of said brush arm biases against said inner wall of said nozzle head to slightly deform a shape of said nozzle head, wherein said dispensing channel is a clearance between said resilient portion of said brush arm and said inner wall of said nozzle head, wherein said dispensing channel is capable of allowing said washing solution passing therethrough towards said brush portion of said brush arm, wherein said brush arm comprises a wiring arm, wherein said resilient portion of said brush arm is formed by bending a tail portion of said wiring arm to form a U-shaped structure, wherein said brush head further comprises a liquid guider, having at least a dispensing hole, mounted on said brush arm, wherein when said resilient portion is slidably inserted into said nozzle head, said liquid guider is attached to said opening of said nozzle to communicate said dispensing hole with said solution cavity for delivering said washing solution from said solution cavity through said dispensing hole; and a brush member provided at said brush portion of said brush arm, thereby, when a squeezing force is applied on said squeezable bottle, said washing solution is released to deliver to said brush member through said dispensing channel of said nozzle head.

5. An interproximal squirt brush, comprising:

a squeezable bottle having a solution cavity for containing a washing solution and a hollow nozzle head having an opening communicating with said solution cavity; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein a diameter of said opening is slightly smaller than a width of said resilient portion of said brush arm such that when said resilient portion of said brush arm is inserted into said opening of said squeezable bottle, said resilient portion of said brush arm biases against said inner wall of said nozzle head to slightly deform a shape of said nozzle head, wherein said dispensing channel is a clearance between said resilient portion of said brush arm and said inner wall of said nozzle head, wherein said dispensing channel is capable of allowing said washing solution passing therethrough towards said brush portion of said brush arm, wherein said brush arm comprises a wiring arm, wherein said resilient portion of said brush arm is formed by bending a tail portion of said wiring arm to form a U-shaped structure and then twisting said tail portion of said wiring arm in continuous "8" shaped, wherein said brush head further comprises a liquid guider, having at least a dispensing hole, mounted on said brush arm, wherein when said resilient portion is slidably inserted into said nozzle head, said liquid guider is attached to said opening of said nozzle to communicate said dispensing hole with said solution cavity for delivering said washing solution from said solution cavity through said dispensing hole; and a brush member provided at said brush portion of said brush arm, thereby, when a squeezing force is applied on said squeezable bottle, said washing solution is released to deliver to said brush member through said dispensing channel of said nozzle head.

6. An interproximal squirt brush, comprising:

a squeezable bottle having a solution cavity for containing a washing solution and a hollow nozzle head having an opening communicating with said solution cavity; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein a diameter of said opening is slightly smaller than a width of said resilient portion of said brush arm such that when said resilient portion of said brush arm is inserted into said opening of said squeezable bottle, said resilient portion of said brush arm biases against said inner wall of said nozzle head to slightly deform a shape of said nozzle head, wherein said dispensing channel is a clearance between said resilient portion of said brush arm and said inner wall of said nozzle head, wherein said dispensing channel is capable of allowing said washing solution passing therethrough towards said brush portion of said brush arm, wherein said brush arm comprises a wiring arm, wherein said resilient portion of said brush arm is formed by twisting a tail portion of said wiring arm into a snake-liked manner, wherein said brush head further comprises a liquid guider, having at least a dispensing hole, mounted on said brush arm, wherein when said resilient portion is slidably inserted into said nozzle head, said liquid guider is attached to said opening of said nozzle to communicate said dispensing hole with said solution cavity for delivering said washing solution from said solution cavity through said dispensing hole; and a brush member provided at said brush portion of said brush arm, thereby, when a squeezing force is applied on said squeezable bottle, said washing solution is released to deliver to said brush member through said dispensing channel of said nozzle head.

7. An interproximal squirt brush, comprising:

a squeezable bottle having a solution cavity for containing a washing solution and a hollow nozzle head having an opening communicating with said solution cavity; and a brush head, comprising:

an elongated brush arm having a brush portion and a resilient portion slidably inserted into said opening of said squeezable bottle for providing an urging force against an inner wall of said nozzle head, so as to hold said brush arm in position, wherein a dispensing channel is formed between said resilient portion of said brush arm and said inner wall of said nozzle head for allowing said washing solution to pass towards said brush portion of said brush arm through said nozzle head, wherein a diameter of said opening is slightly smaller than a width of said resilient portion of said brush arm such that when said resilient portion of said brush arm is inserted into said opening of said squeezable bottle, said resilient portion of said brush arm biases against said inner wall of said nozzle head to slightly deform a shape of said nozzle head, wherein said dispensing channel is a clearance between said resilient portion of said brush arm and said inner wall of said nozzle head, wherein said dispensing channel is capable of allowing said washing solution passing therethrough towards said brush portion of said brush arm, wherein said brush arm comprises a wiring arm, wherein said resilient portion of said brush arm is formed by bending a tail portion of said wiring arm into a V-liked manner, wherein said brush head further comprises a liquid guider, having at least a dispensing hole, mounted on said brush arm, wherein when said resilient portion is slidably inserted into said nozzle head, said liquid guider is attached to said opening of said nozzle to communicate said dispensing hole with said solution cavity for delivering said washing solution from said solution cavity through said dispensing hole; and a brush member provided at said brush portion of said brush arm, thereby, when a squeezing force is applied on said squeezable bottle, said washing solution is released to deliver to said brush member through said dispensing channel of said nozzle head.

* * * * *